US006124488A

United States Patent [19]
Gruter et al.

[11] Patent Number: 6,124,488
[45] Date of Patent: Sep. 26, 2000

[54] CYCLOPENTADIENE COMPOUND SUBSTITUTED WITH BRANCHED ALKYL GROUPS

[75] Inventors: Gerardus J. M. Gruter, Maastricht, Netherlands; Johannes A. M. van Beek, Mountain View, Calif.; Richard Green, Geleen; Edwin G. IJpeij, Sittard, both of Netherlands

[73] Assignee: DSM N.V., Heerlen, Netherlands

[21] Appl. No.: 09/184,065

[22] Filed: Nov. 2, 1998

Related U.S. Application Data

[63] Continuation of application No. PCT/NL97/00233, Apr. 28, 1997.

[30] Foreign Application Priority Data

May 3, 1996 [NL] Netherlands .......................... 1003007

[51] Int. Cl.⁷ ............................... C07F 17/00; C07F 7/00
[52] U.S. Cl. ............................. 556/53; 556/11; 556/43; 556/58; 556/136; 556/140; 534/15; 526/127; 526/160; 526/943; 502/103; 502/117; 585/350
[58] Field of Search ............................. 585/350; 556/11, 556/43, 53, 58, 136, 140; 502/103, 117; 526/127, 160, 943; 534/15

[56] References Cited

U.S. PATENT DOCUMENTS

| | | | |
|---|---|---|---|
| 2,916,503 | 12/1959 | Kozikowski | 260/429 |
| 5,563,284 | 10/1996 | Frey et al. | 556/53 |

FOREIGN PATENT DOCUMENTS

| | | |
|---|---|---|
| 0 416 815 A2 | 3/1991 | European Pat. Off. . |
| 0 728 724 | 8/1996 | European Pat. Off. . |
| 0 728 769 A1 | 8/1996 | European Pat. Off. . |
| 0 728 770 A1 | 8/1996 | European Pat. Off. . |
| 43 03 647 | 8/1994 | Germany . |
| 864198 | 3/1961 | United Kingdom . |
| WO 95/00562A | 1/1995 | WIPO . |
| WO 96/13529 | 5/1996 | WIPO . |

OTHER PUBLICATIONS

Szymoniak et al., "New Heterodifunctional Ligands for Organotransiton–Metal Chemistry . . . ", Journal of Organic Chemistry, 1990, vol. 55, pp. 1429–1432.

Ying Mu et al., "Use of Alkane Elimination in the One–step Synthesis of Organoscandium Complexes Containing a New Multidentate Cyclopentadienyl Ligand", Organometallics, 1996, vol. 15, pp. 2720–2726.

Chemical Abstracts, vol. 123, No. 13 (Sep. 1995), Abstract No. 169881g.

Weinheim DE, K. Hafner et al., "Synthesen und Reaktionen von Fulvenaldehyden", Chemische Berichte, 1963, vol. 661, pp. 52–75.

G. Kresze et al., "Substitierte Cyclopentadiene und ihre Diels–Alder–Reaktionen", Chemische Berichte, 1963, vol. 666, pp. 45–53.

Krut'ko, D.P. et al., "Tetramethyl(2–methyltioethyl)cyclopentadienyl Complexes of Zirconium(IV): Synthesis, . . . Solutions", Russian Chemical Bulletin, 1996, vol. 45, No. 4, pp. 940–949.

Ulrich Siemeling, "$C_5Me_4(CH_2)_3OMe$: A Tentacle–bearing Cyclopentadienyl Ligand and Its Use in Complex Chemistry", J. Chem. Soc. Commun., 1992, vol. 18, pp. 1335–1336.

R. Allen Williams et al., 'Encapsulated Alkaline–Earth Metallocenes. Synthesis, Solution Behavior, and Solid–State Structures of . . .,' Journal of the American Chemical Society, vol. 113, No. 13, Jun. 19, 1991, pp 4843–4851.

Clifford G. Venier et al., 'D–tert–butylcyclopentadiene and Tri–tert–butylcyclopentadiene', Journal of the American Chemical Society, vol. 112, No. 7, Mar. 28, 1990.

Eckehard V. Dehmlow et al., 'Phase Transfer Catalyzed tert–Alkylations of Cyclopentadiene and Indene: Indications for Set Processess', Tetrahedron Letters, vol. 32, No. 41, Oct. 1991.

R.H. Chung, et al., "1–Isopropyl–4–methylenebicyclo [3.1.0]hex–2–ene. Synthesis and reactions", J. Amer. Chem. Soc., vol. 94(7), pp. 2183–2187, 1972.

G. Moran et al., "Formation of a fulvene by trimerisation of an alkyne at a Rhodium centre; . . . ", Journal of Organometallic Chemistry, vol. 250, 1983, pp. C15–C20.

T. Jeffrey Clark et al., "Regioselective synthesis of dialkyl–1, 3–cyclopentadienes via novel 2–alkyl–6,6–dialkylfulvenes" Synlett (1990), (10), 589–90.

T. Leigh, "Ferrocene Derivatives containing Tertiary Alkyl Groups. Synthesis by the Friedel–Crafts and Other Methods", Journal of the Chemical Society, 1964, Letchworth GB, pp. 3294–3302.

R.R. Schrock et al., "Formation of Cyclopentadienyl Complexes from Tungstenacyclobutadiene Complexes and the X–ray Crystal Structure of an eta–3–Cyclopropenyl Complex, W[C(CMe3)C(Me)C(Me)] (Me2NCH2CH2NMe2)CI3", Organometallics, vol. 3, No. 10, 1984, pp. 1574–1583.

H. Van Der Heijden et al., "Reactions of the Trimetallic Neopentylidene Complex [{CI2(MeOCH2CH20Me)Ta(mu–CCMe3)}2Zn(mu–CI)2] with Alkynes. A Structural Study of [(eta5–C5(t–Bu)(CH2CMe3)2(CH2CMe2CH2)2)TaC12]", Organometallics, vol. 4, No. 10, 1985, pp. 1847–1853.

Sappa Enrico et al., "Mass spectral investigations on sigma–pi bonded binuclear alkyne–carbonyl derivatives of iron. Fe2(CO)5/C2RR')3(C)) and Fe2(CO)6/RR')3 complexes", Chemical Abstracts, vol. 91, No. 9 (Aug. 27, 1979, Abstract No. 73791x.

Bensley, Jr. et al.; "Synthesis of $[C_5(CH_3)_4H]$ $CH_2CH_2P(C^6H_5)_2$: A Novel . . . Functionality"; J. Org. Chem. 1988, vol. 53, pp. 4417–4419.

Balakrishnan, P.V. et al; (Pentamethyl–cyclopentadiene) palladium Complexes; J. Chem. Soc. (A), Inorg. Phys. Theor.; 1971, pp. 1721–1725.

*Primary Examiner*—Porfirio Nazario-Gonzalez
*Attorney, Agent, or Firm*—Pillsbury Madison & Sutro Intellectual Property Group

[57] ABSTRACT

Polysubstituted cyclopentadiene compound, in which at least one substituent is of the form $-RDR'_n$, in which R is a bonding group, D is a hetero atom selected from group 15 or 16 of the Periodic System of the Elements, R' is a substituent and n is the number of R' groups bonded to D, and in that at least one further substituent is a branched alkyl group.

20 Claims, No Drawings

CYCLOPENTADIENE COMPOUND SUBSTITUTED WITH BRANCHED ALKYL GROUPS

This is a Continuation of International Appln. No. PCT/NL/97/00233 filed Apr. 28, 1997 which designated the U.S.

The invention relates to a polysubstituted cyclopentadiene compound.

Cyclopentadiene compounds are generally used as ligands in metal complexes which are active as catalyst components, in particular for the polymerization of olefins.

In J. of Organomet. Chem., 479 (1994), 1–29 an overview is provided of the influence of the substituents on cyclopentadiene as a ligand in metal complexes. Here it is observed, on the one hand, that the chemical and physical properties of metal complexes can be varied over a wide range by the specific choice of the substituents on the cyclopentadiene ring. On the other hand, it is stated that no predictions can be made concerning the effect to be expected of specific substituents. Depending on the metal, its valency state and the ligands used, the complexes prove to be of varying suitability for particular applications. Polyolefin polymerizations are often copolymerizations of α-olefins, for example ethene or propene with one or more other olefins and/or other vinyl monomers, including vinyl-aromatic monomers. The cyclopentadiene compounds most often used are unsubstituted cyclopentadiene or cycdopentadiene substituted with one to five methyl groups. However, when used as a ligand in metal complexes and in particular in those where the metal is not in the highest valency state (the metal therefore, for example, being Ti(III), Hf(III), Zr(III) or V(IV)) these cyclopentadiene compounds are found to provide catalyst components, producing copolymers with an adverse combination of molecular weight and comonomer incorporation, when used as a catalyst compound for polymerisation of olefins. This implies that polymerization under conditions which favour the production of copolymers having a higher molecular weight leads to polymers having a relatively low comonomer incorporation. Incidentally, the said review article in J. of Organomet. Chem. from 1994 even states that "An important feature of these catalyst systems is that tetravalent Ti centres are required for catalytic activity". Note should be taken, in this context, of the fact that Ti is exemplary for the metals which are suitable as a metal in the conventional cyclopentadienyl-substituted metal complexes.

Hereinafter, cyclopentadiene will be abbreviated to Cp. The same abbreviation will be used for a cyclopentadienyl group if it is clear, from the context, whether cyclopentadiene itself or its anion is meant.

The term olefins here and hereinafter refers to α-olefins, diolefins and other unsaturated monomers. If the term polymerization of olefins is used, this hereinafter refers both to the polymerization of a single type of olefinic monomer and to the copolymerization of two or more olefins.

The object of the invention is to provide Cp compounds which, when used as a ligand in a metal complex in which the metal is not in the highest valency state, provide catalysts which can be used to produce copolymers having a more favourable combination of molecular weight and comonomer incorporation.

This object is achieved, according to the invention, by at least one substituent being of the form -RDR'$_n$, in which R is a bonding group between the Cp and the DR'$_n$ group, D is a hetero atom selected from group 15 or 16 of the Periodic System of the Elements, R' is a substituent and n is the number of R' groups bonded to D, and by at least one further substituent being a branched alkyl group.

Surprisingly, Cp compounds substituted in this manner, when used as a ligand in the above-described metal complexes, are found to provide catalyst components, producing copolymers having a higher incorporation of comonomers in the case of ethene copolymerization, with the same molecular weight, than the known compounds, when used as catalyst component for the polymerisation of olefins. Preferably, the compound contains at least two branched alkyl groups as a substituent, because this affords a further improvement in the ratio between molecular weight and comonomer incorporation.

Corresponding complexes in which the Cp compound is not substituted in the manner described prove unstable or, if they have been stabilized in some other way, are found to provide less active catalysts than the complexes containing substituted Cp compounds according to the invention, in particular in the case of the polymerization of α-olefins.

Moreover, the Cp compounds according to the invention are found to be able to stabilize highly reactive intermediates such as organometal hydrides, organometal borohydrides, organometal alkyls and organometal cations. Furthermore the metal complexes containing Cp compounds according to the invention prove suitable as stable and volatile precursors for the use in metal chemical vapour deposition.

J. of Organomet. Chem. 486 (1995), 287–289 discloses tetramethylcyclopentadiene with ethyl dimethylamine as the fifth substituent. This publication provides no indication or suggestion whatsoever of the suitability of the Cp compounds according to the invention as ligands in metal complexes which, as a catalyst component, effect improved comonomer incorporation in the case of olefin copolymerizations. This applies more strongly, in particular, to this effect with complexes of metals which are not in the highest valency state.

As a matter of fact, the Cp compounds according to the invention can also, to good effect, be used as a ligand on metals which actually are in their highest valency state.

The branched alkyl groups can be either identical or different. Preferably, the substituted Cp compound contains 1–4 branched alkyl groups as a substituent. As the number of substituents in the form of branched alkyl groups increases, the activity of a metal complex in which the Cp compounds thus substituted are present as a ligand is found to increase when used as a catalyst component for the polymerization of α-olefins. The branched alkyl groups do not contain any hetero atoms from group 16 of the Periodic System of the Elements. Particularly suitable branched alkyl groups are, for example, 2-propyl, 2-butyl, 2-pentyl, 2-hexyl, 2-heptyl, 2-octyl, 2-nonyl, 2-decyl, 3-pentyl, 3-hexyl, 3-heptyl, 3-octyl, 3-nonyl, 3-decyl, 3-undecyl, 3-dodecyl, 2-(3-methylbutyl), 2-(3-methylpentyl), 2-(4-methylpentyl), 3-(2-methylpentyl), 2-(3,3-dimethylbutyl), 2-(3-ethylpentyl), 2-(3-methylhexyl), 2-(4-methylhexyl), 2-(5-methylhexyl), 2-(3,3-dimethylpentyl), 2-(4,4-dimethylpentyl), 3-(4-methylhexyl), 3-(5-methylhexyl), 3-(2,4-dimethylpentyl), 3-(2-methylhexyl), 3-(4,4-dimethylpentyl), 1-(2-ethylbutyl), 1-(2-methyl-3-chloropropyl), 2-(1-chloropropyl), 1-(3-methylbutyl), 4-(2-methylbutenyl), 1-(2-methylpropyl), 1-(2-ethylbutyl), 1-(3-chloro-2-methylpropyl), 2-(1-chloropropyl), 1-(2-methylbutenyl), 1-(2-methylpropyl), cyclopentyl and cyclohexyl. Cp compounds disubstituted or trisubstituted with branched alkyl groups are preferred.

In addition to these branched alkyl groups, whose presence is required within the scope of the invention, further substituents may also be present, for example linear alkyl groups, alkenyl and aralkyl groups. It is also possible for these to contain, apart from carbon and hydrogen, one or more hetero atoms from groups 14–17 of the Periodic System of the Elements, for example O, N, Si or F. Examples of suitable groups are methyl, ethyl, n-butyl, n-pentyl, n-hexyl and n-octyl, benzyl, phenyl, p-tolyl and trimethylsilyl.

For the Periodic System, see the new IUPAC notation to be found on the inside of the cover of the Handbook of Chemistry and Physics, 70th edition, 1989/1990.

Substituted Cp compounds can, for instance, be prepared by reacting a halide of the substituting compound in a mixture of Cp compound and an aqueous solution of a base in the presence of a phase transfer catalyst.

The term Cp compounds refers to Cp itself and Cp already substituted in 1 to 3 positions, with the option of two substituents forming a closed ring. By means of the method according to the invention it is thus possible to convert unsubstituted compounds into singly or multiply substituted ones, but it is also possible for mono- or polysubstituted compounds derived from Cp to be substituted further, whereupon ring closure is an additional option. It is possible to use a virtually equivalent quantity with respect to the Cp compound of the halogenated substituting compound. An equivalent quantity is understood as a quantity in moles which corresponds to the desired substitution multiplicity, for example 2 mol per mole of Cp compound, if disubstitution with the substituent in question is intended.

Depending on the size and the associated steric hindrance of the substituting compounds it is possible to obtain trisubstituted to pentasubstituted Cp compounds. If a reaction with a tertiary halide of a substituting compound is carried out, as a rule only trisubstituted Cp compounds can be obtained, whereas with a primary and secondary halide of a substituting compound it is generally possible to achieve tetra- and often even pentasubstitution.

Particularly suitable branched alkyl substituents have already been specified hereinabove. The number of substituents thus introduced is 1–4 for the Cp compounds according to the invention, in addition to possible other groups to be substituted in positions still free, as defined above.

The substituents are preferably used in the method in the form of their halides and more preferably in the form of their bromides. If bromides are used a smaller quantity of phase transfer catalyst is found to be sufficient, and a higher yield of the compound aimed for is found to be achieved.

By means of this method it is also possible, without intermediate isolation or purification, to obtain Cp compounds which are substituted with specific combinations of substituents. Thus, for example, disubstitution with the aid of a certain halide of a substituting compound can first be carried out and in the same reaction mixture a third substitution can be carried out with a different substituent, by adding a second, different halide of a substituting compound to the mixture after a certain time. This can be repeated, so that it is also possible to prepare Cp derivatives having three or more different substituents.

The substitution takes place in a mixture of the Cp compound and an aqueous solution of a base. The concentration of the base in the solution is in the range between 20 and 80 wt. %. Hydroxides of an alkali metal, for example K or Na are highly suitable as a base. The base is present in an amount of 5–60 mol, preferably 6–30 mol, per mole of Cp compound. It was found that the reaction time can be considerably shortened if the solution of the base is refreshed during the reaction is, for example by first mixing, the solution with the other components of the reaction mixture and after some time separating the aqueous phase and replacing it by a fresh quantity of the solution of the base. The substitution takes place at atmospheric or elevated pressure, for example up to 100 Mpa, particularly when volatile components are present. The temperature at which the reaction takes place can vary between wide limits, for example from −20 to 120° C., preferably between 10 and 50° C. Initiating the reaction at room temperature is suitable, as a rule, whereupon the temperature of the reaction mixture may rise as a result of the heat liberated in the course of the reactions which occur.

The substitution takes place in the presence of a phase transfer catalyst which is able to transfer OH-ions from the aqueous phase to the organic phase containing Cp compound and halide, the OH-ions reacting in the organic phase with an H-atom which can be split off from the Cp compound. Possible phase transfer catalysts to be used are quaternary ammonium, phosphonium, arsonium, stibonium, bismuthonium, and tertiary sulphonium salts. More preferably, ammonium and phosphonium salts are used, for example tricaprylmethylammonium chloride, commercially available under the name Aliquat 336 (Fluka AG, Switzerland; General Mills Co., USA) and Adogen 464 (Aldrich Chemical Co., USA). Compounds such as benzyltriethylammonium chloride (TEBA) or benzyltriethylammonium bromide (TEBA-Br), benzyltrimethylammonium chloride, benzyltrimethylammonium bromide or benzyltrimethylammonium hydroxide (Triton B), tetra-n-butylammonium chloride, tetra-n-butylammonium bromide, tetra-n-butylammonium iodide, tetra-n-butylammonium hydrogen sulphate or tetra-n-butylammonium hydroxide and cetyltrimethylammonium bromide or cetyltrimethylammonium chloride, benzyltributyl-, tetra-n-pentyl-, tetra-n-hexyl- and trioctylpropylammonium chlorides and their bromides are likewise suitable. Usable phosphonium salts include, for example, tributylhexadecylphosphonium bromide, ethyltriphenylphosphonium bromide, tetraphenylphosphonium chloride, benzyltriphenylphosphonium iodide and tetrabutylphosphonium chloride. Crown ethers and cryptands can also be used as a phase transfer catalyst, for example 15-crown-5,18-crown-6, dibenzol8-crown-6, dicyclohexano-18-crown-6, 4,7,13,16,21-pentaoxa-1,10-diazabicyclo[8.8.5]tricosane (Kryptofix 221), 4,7,13,18-tetraoxa-1,10-diazabicyclo[8.5.5]eicosane (Kryptofix 211) and 4,7,13,16,21,24-hexaoxa-1,10-diazabicyclo[8.8.8]-hexacosane ("[2.2.2]") and its benzo derivative Kryptofix 222 B. Polyethers such as ethers of ethylene glycols can also be used as a phase transfer catalyst. Quaternary ammonium salts, phosphonium salts, phosphoric acid triamides, crown ethers, polyethers and cryptands can also be used on supports such as, for example, on a crosslinked polystyrene or another polymer. The phase transfer catalysts are used in an amount of 0.01–2, preferably 0.05–1 equivalents on the basis of the amount of Cp compound.

In the implementation of the method, the components can be added to the reactor in various sequences.

After the reaction is complete, the aqueous phase and the organic phase which contains the Cp compound are separated. When necessary, the Cp compound is then obtained from the organic phase by fractional distillation.

The Cp compound thus substituted then undergoes substitution with a group of the form -RDR'$_n$.

The R group forms the link between the Cp and the DR'$_n$ group. The length of the shortest link between the Cp and D is critical insofar as it is determining, when the Cp compound is used as a ligand in a metal complex, for the accessibility of the metal by the DR'$_n$ group in order thus to achieve the desired intramolecular coordination. Too small a length of the R group (or bridge) may mean that owing to ring tension the $DR'_n$ group cannot coordinate effectively. R therefore has a length of at least one atom.

The R' groups may each, separately, be a hydrocarbon radical containing 1–20 carbon atoms (such as alkyl, aryl, aralkyl and the like). Examples of such hydrocarbon radicals are methyl, ethyl, propyl, butyl, hexyl, decyl, phenyl, benzyl and p-tolyl. R' can also be a substituent which, in addition to or instead of, carbon and/or hydrogen contains one or more hetero atoms from group 14–16 of the Periodic System of the Elements. For example, a substituent can be an N-, O-, and/or Si-containing group.

The R group can be a hydrocarbon group containing 1–20 carbon atoms (such as alkylidene, arylidene, arylalkylidene and the like). Examples of such groups are methylene, ethylene, propylene, butylene, phenylene, with or without a substituted side chain. Preferably, the R group has the following structure:

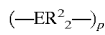

$$(-ER^2_2-)_p$$

where p=1–4 and E is an atom from group 14 of the Periodic System of the Elements. The $R^2$ groups can each be H or a group as defined for R'.

The main chain of the R group may consequently, in addition to carbon, also contain silicon or germanium. Examples of such R groups are: dialkylsilylene, dialkylgermylene, tetraalkyldisilylene or dialkylsilaethylene $(-(CH_2)(SiR^2_2)-)$. The alkyl groups ($R^2$) in such a group preferably contain 1–4 C atoms and are, more preferably, a methyl or ethyl group.

The $DR'_n$ group consists of a hetero atom D, selected from group 15 or 16 of the Periodic System of the Elements, and one or more substituent(s) R' bound to D. The number of R' groups (n) is linked to the type of the hetero atom D, in the sense that n=2 if D is from group 15 and that n=1 if D is from group 16. Preferably, the hetero atom D is selected from the group consisting of nitrogen (N), oxygen (O), phosphorus (P) or sulphur (S); more preferably, the hetero atom is nitrogen (N) or phosphorus (P). Likewise preferably, the R' group is an alkyl, more preferably an n-alkyl group containing 1–20 C atoms. More preferably, the R' group is an n-alkyl containing 1–10 C atoms. Another possibility is for two R' groups in the $DR'_n$ group to be joined together to give a ring-shaped structure (so that the $DR'_n$ group may be a pyrrolidinyl group). The $DR'_n$ group can bind coordinatively to a metal.

For the purpose of preparing such Cp compounds, the Cp compound substituted as described above can then be substituted with a group in the form of $-RDR'_n$, for example in accordance with the following synthesis route.

During a first step of this route a substituted Cp compound is deprotonated by reaction with a base, sodium or potassium.

Possible bases to be used are, for example, organolithium compounds ($R^3Li$) or organomagnesium compounds ($R^3MgX$), where $R^3$ is an alkyl, aryl or aralkyl group, and X is a halide, for example n-butyllithium or i-propylmagnesium chloride. Potassium hydride, sodium hydride, inorganic bases, for example NaOH and KOH, and alcoholates of Li, K and Na can likewise be used as a base. Mixtures of the abovementioned compounds can also be used.

This reaction can be carried out in a polar dispersing agent, for example an ether. Examples of suitable ethers are tetrahydrofuran (THF) or dibutyl ether. Nonpolar solvents such as, for example, toluene, can likewise be employed.

Subsequently, during a second step of the synthesis route, the cyclopentadienyl anion formed reacts with a compound according to the formula ($R'_nD$-R-Y) or (X-R-Sul), in which D, R, R' and n are as defined hereinabove. Y is a halogen atom (X) or a sulphonyl group (Sul). Halogen atoms X to be mentioned are chlorine, bromine and iodine. Preferably, the halogen atom X is a chlorine atom or bromine atom. The sulphonyl group takes the form $-OSO_2R_6$, in which $R^6$ is a hydrocarbon radical containing 1–20 carbon atoms, for example alkyl, aryl, aralkyl. Examples of such hydrocarbon radicals are butane, pentane, hexane, benzene, naphthalene. Instead of, or in addition to, carbon and/or hydrogen, $R^6$ may also contain one or more hetero atoms from groups 14–17 of the Periodic System of the Elements, such as N, O, Si or F. Examples of sulphonyl groups are: phenylmethanesulphonyl, benzenesulphonyl, 1-butanesulphonyl, 2,5-dichlorobenzenesulphonyl, 5-dimethylamino-1-naphthalenesulphonyl, pentafluorobenzenesulphonyl, p-toluenesulphonyl, trichloromethanesulphonyl, trifluoromethanesulphonyl, 2,4,6-triisopropylbenzenesulphonyl, 2,4,6-trimethylbenzenesulphonyl, 2-mesitylenesulphonyl, methanesulphonyl, 4-methoxybenzenesulphonyl, 1-naphthalenesulphonyl, 2-naphthalenesulphonyl, ethanesulphonyl, 4-fluorobenzenesulphonyl and 1-hexadecanesulphonyl. Preferably, the sulphonyl group is p-toluenesulphonyl or trifluoromethanesulphonyl.

If D is a nitrogen atom and Y is a sulphonyl group, the compound according to the formula ($R'_nD$-R-Y) is formed in situ by reaction of an aminoalcohol compound ($R'_2NR-OH$) with a base (such as defined hereinabove), potassium or sodium, followed by a reaction with a sulphonyl halide (Sul-X).

The second reaction step can likewise be carried out in a polar dispersing agent such as described for the first step. The temperature at which the reactions are carried out is between −60 and 80° C. Reactions with X-R-Sul and with $R'_nD$-R-Y, in which Y is Br or I, are as a rule carried out at a temperature between −20 and 20° C. Reactions with $R'_nD$-R-Y, in which Y is Cl, are as a rule carried out at a higher temperature (10 to 80° C.). The upper limit for the temperature at which the reactions are carried out is determined, inter alia, by the boiling point of the compound $R'_nD$-R-Y and that of the solvent used.

After the reaction with a compound according to the formula (X-R-Sul) a further reaction is carried out with $LiDR'_n$ or $HDR'_n$ to replace X by a $DR'_n$ functionality. To this end a reaction is carried out, possibly in the same dispersing agent as mentioned above, at 20 to 80° C.

In the synthesis process according to the invention it is possible for geminal products to be formed in part. A geminal substitution is a substitution in which the number of substituents increases by 1 but in which the number of substituted carbon atoms does not increase. The amount of geminal products formed is low if the synthesis is carried out starting from a substituted Cp compound having 1 substituent and increases as the substituted Cp compound contains more substituents. Geminally substituted Cp compounds are not suitable for use as a ligand and are not considered to be within the scope of the invention. In the presence of sterically large substituents in the substituted Cp compound no or virtually no geminal products are formed. Examples of sterically large substituents are secondary or tertiary alkyl substituents. The amount of geminal product formed is also low if the second step of the reaction is carried out under the influence of a Lewis base whose conjugated acid has a dissociation constant with a $pK_a$ of less than or equal to −2.5. The p$K_a$ values are based on D. D. Perrin: Dissociation Constants of Organic Bases in Aqueous Solution, International Union of Pure and Applied Chemistry, Butterworths, London 1965. The values have been determined in aqueous $H_2SO_4$ solution. Ethers may be mentioned as an example of suitable weak Lewis bases.

If geminal products have been formed during the process according to the invention, these products can be separated in a simple manner from the non-geminal products by converting the mixture of geminal and non-geminal substituted products into a salt, by reaction with potassium, sodium or a base, the salt then being washed with a dispersing agent in which the salt of the non-geminal products is insoluble or sparingly soluble. Bases which can be used include the compounds as mentioned above. Suitable dispersing agents are nonpolar dispersing agents such as alkanes. Examples of suitable alkanes are heptane and hexane.

Metal complexes which are catalytically active if one of their ligands is a compound according to the invention are complexes of metals from groups 4–10 of the Periodic System of the Elements and lanthanides. In this context, complexes of metals from groups 4 and 5 are preferably used as a catalyst component for polymerizing olefins, complexes of metals from groups 6 and 7 in addition also for metathesis and ring-opening metathesis polymerizations, and complexes of metals from groups 8–10 for olefin copolymerizations with polar comonomers, hydrogenations and carbonylations. Particularly suitable for the polymerization of olefins are such metal complexes in which the metal is chosen from the group consisting of Ti, Zr, Hf, V and Cr.

Especially if the metals, in particular the five mentioned individually hereinabove, are not in their highest valency state, the Cp compounds are found to provide excellent stability of the complex formed without blocking the active sites, the catalytic activity consequently being higher than when other Cp compounds are used. The invention therefore also relates to metal complexes in which at least one of the ligands is a substituted Cp compound according to the invention and in which, preferably, the metal is in a valency state below the highest valency state, and to the use of such metal complexes as a catalyst component for copolymerizing α-olefins with other α-olefins and in general vinyl monomers and in particular vinylaromatic monomers.

Vinyl-aromatic monomers which are incorporated effectively by means of these catalysts include styrene, chlorostyrene, n-butylstyrene, p-vinyltoluene and in particular styrene.

The synthesis of metal complexes containing the above-described specific Cp compounds as a ligand may take place according to the methods known per se for this purpose. The use of these Cp compounds does not require any adaptations of said known methods.

The polymerization of α-olefins, for example ethene, propene, butene, hexene, octene and mixtures thereof and combinations with dienes can be carried out in the presence of the metal complexes containing the cyclopentadienyl compounds according to the invention as a ligand. Particularly suitable for this purpose are the complexes of transition metals, not in their highest valency state, in which just one of the cyclopentadienyl compounds according to the invention is present as a ligand, and in which the metal is cationic during the polymerization. These polymerizations can be carried out in the manner known for this purpose, and the use of the metal complexes as a catalyst component does not require any significant adaptation of these methods. The known polymerizations are carried out in suspension, solution, emulsion, gas phase or as a bulk polymerization. It is customary to use, as a cocatalyst, an organometallic compound, the metal being selected from group 1, 2, 12 or 13 of the Periodic System of the Elements. Examples to be mentioned include alkylaluminoxanes (such as methylaluminoxanes), tris(pentafluorophenyl) borane, dimethylanilinium tetra(pentafluorophenyl) borate or mixtures thereof. The polymerizations are carried out at temperatures between −50° C. and +350° C., more in particular between 25 and 250° C. Pressures used are generally between atmospheric pressure and 250 MPa, for bulk polymerizations more in particular between 50 and 250 MPa, for the other polymerization processes between 0.5 and 25 MPa. Dispersing agents and solvents to be used include, for example, hydrocarbons such as pentane, heptane and mixtures thereof. Aromatic, optionally perfluorinated hydrocarbons are also suitable. The monomer to be employed in the polymerization can also be used as a dispersing agent or solvent.

The invention will be explained with reference to the following examples, but is not limited thereto.

The synthesis of the catalyst components was performed under dry Ar or $N_2$.

Characterization of the products obtained involves the following analytical methods.

Gas chromatography (GC) was carried out on a Hewlett-Packard 5890 series II with an HP crosslinked methyl silicon gum (25 m×0.32 mm×1.05 μm) column. Combined gas chromatography/mass spectrometry (GC-MS) was carried out with a Fisons MD800 equipped with a quadrupole mass detector, autoinjector Fisons AS800 and CPSil8 column (30 m×0.25 mm×1 μm, low bleed). NMR was carried out on a Bruker ACP200 ($^1H$=200 MHz; $^{13}C$=50 MHz) or Bruker ARX400 ($^1H$=400 MHz; $^{13}C$=100 MHz). To characterize metal complexes, use was made of a Kratos MS80 or alternatively a Finnigan Mat 4610 mass spectrometer.

EXAMPLE I

Preparation of di(2-propyl)cyclopentadiene

In a double-walled reactor having a volume of 200 mL, provided with baffles, condenser, top stirrer, thermometer and dropping funnel, 180 g of clear 50% strength NaOH (2.25 mol), 9.5 g of Aliquat 336 (23 mmol) and 15 g (0.227 mol) of freshly cracked cyclopentadiene were combined. The reaction mixture was stirred turbulently at a speed of 1385 rpm for a few minutes. Then 56 g of 2-propyl bromide (0.46 mol) were added, cooling with water taking place at the same time. A few minutes after the addition of the 2-propylbromide the temperature rose by approximately 10° C. Stirring then continued for 6 hours at 50° C. GC was used to show that at that instant 92% of di(2-propyl)cyclopentadiene were present in the mixture of di- and tri(2-propyl)cyclopentadiene. The product was distilled at 10 mbar and 70° C. After distillation, 25.35 g of di(2-propyl)cyclopentadiene were obtained. Characterization took place with the aid of GC, GC-MS, $^{13}C$- and $^1H$-NMR.

EXAMPLE II

Preparation of tri(2-propyl)cyclopentadiene

In a double-walled reactor having a volume of 200 mL, provided with baffles, condenser, top stirrer, thermometer and dropping funnel, 180 g of clear 50% strength NaOH (2.25 mol), 9.5 g of Aliquat 336 (23 mmol) and 15 g (0.227 mol) of freshly cracked cyclopentadiene were combined. The reaction mixture was stirred turbulently at a speed of 1385 rpm for a few minutes. Then 84 g of 2-propyl bromide (0.68 mol) were added, cooling with water taking place at the same time. A few minutes after the addition of the 2-propyl bromide the temperature rose by approximately 10° C. GC was used to show that approximately 30 minutes after the addition of all the 2-propyl bromide (monosubstituted) 2-propylcyclopentadiene had been formed. The reaction mixture was then warmed to 50° C. After 2 hours, stirring was stopped and phase separation was awaited. The water layer was drawn off, and 180 g (2.25 mol) of fresh 50% strength NaOH were added. Stirring then continued for a further one hour at 50° C. GC was used to show that at that instant between 90 and 95% of tri(2-propyl) cyclopentadiene were present in the mixture of di-, tri- and tetra(2-propyl)cyclopentadiene. The product was distilled at 1.3 mbar and 77–78° C. After distillation, 31.9 g of tri(2-propyl)cyclopentadiene were obtained. Characterization took place with the aid of GC, GC-MS, $^{13}$C- and $^{1}$H-NMR.

EXAMPLE III

Preparation of tetra(2-propyl)cyclopentadiene

Analogous to Example II, but 114 g of 2-propyl bromide (0.93 mol) were now added, and after 7 hours the water layer was replaced a second time. At the same time, a further 5 g (12 mmol) of Aliquat 336 were added. Heating then took place for 16 hours at 55° C. GC was used to show that at that instant 85% of tetra(2-propyl)cyclopentadiene were present in the mixture of tri- and tetra(2-propyl)cyclopentadiene. The product was distilled at 1.0 mbar and 88–90° C. After distillation, 34.9 g of tetra(2-propyl)cyclopentadiene were obtained. Characterization took place with the aid of GC, GC-MS, $^{13}$C- and $^{1}$H-NMR.

EXAMPLE IV

Preparation of di(cyclohexyl)cyclopentadiene

A double-walled reactor having a volume of 1 L, provided with baffles, condenser, top stirrer, thermometer and dropping funnel was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred turbulently for a few minutes. Then 172 g of cyclohexyl bromide (1.05 mol) were added, cooling with water taking place at the same time. After 2 hours' stirring at room temperature the reaction mixture was warmed to 70° C., followed by a further 6 hours' stirring. GC was used to show that at that instant 79% of di(cyclohexyl)cyclopentadiene were present. The product was distilled at 0.04 mbar and 110–120° C. After distillation, 73.6 g of di(cyclohexyl) cyclopentadiene were obtained. Characterization took place with the aid of GC, GC-MS, $^{13}$C- and $^{1}$H-NMR.

EXAMPLE V

Preparation of di- and tri(3-pentyl)cyclopentadiene

A double-walled reactor having a volume of 1 L, provided with baffles, condenser, top stirrer, thermometer and dropping funnel was charged with 430 g (5.4 mol) of clear 50% strength NaOH. Then 23 g of Aliquat 336 (57 mmol) and 27 g (0.41 mol) of freshly cracked cyclopentadiene were added. The reaction mixture was stirred turbulently for a few minutes. Then 150 g of 3-pentyl bromide (1.0 mol) were added over a period of 1 hour, cooling with water taking place at the same time. After 1 hour's stirring at room temperature the reaction mixture was warmed to 70° C., followed by a further 3 hours' stirring. Stirring was stopped and phase separation was awaited. The water layer was drawn off and 540 g (6.70 mol) of fresh 50% strength NaOH were added, followed by a further 4 hours' stirring at 70° C. GC was used to show that at that instant the mixture consisted of di- and tri(3-pentyl)cyclopentadiene (approximately 3:2). The products were distilled at 0.2 mbar, 51° C. and 0.2 mbar, 77–80° C., respectively. After distillation, 32 g of di-and 18 g of tri(3-pentyl) cyclopentadiene were obtained. Characterization took place with the aid of GC, GC-MS, $^{13}$C- and $^{1}$H-NMR.

EXAMPLE VI

Preparation of tri(cyclohexyl)cyclopentadiene

A double-walled reactor having a volume of 1 L, provided with baffles, condenser, top stirrer, thermometer and dropping funnel was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred turbulently for a few minutes. Then 256 g of cyclohexyl bromide (1.57 mol) were added, cooling with water taking place at the same time. After 1 hour's stirring at room temperature the reaction mixture was warmed to 70° C., followed by a further 2 hours' stirring. After 2 hours, stirring was stopped and phase separation was awaited. The water layer was drawn off and 600 g (7.5 mol) of fresh 50% strength NaOH were added, followed by a further 4 hours' stirring at 70° C. GC was used to show that at that instant 10% of di- and 90% of tri(cyclohexyl)cyclopentadiene were present in the mixture. The product was distilled at 0.04 mbar and 130° C. After distillation, 87.4 g of tri(cyclohexyl) cyclopentadiene were obtained. Characterization took place with the aid of GC, GC-MS, $^{13}$C- and $^{1}$H-NMR.

EXAMPLE VII

Preparation of di(2-butyl)cyclopentadiene

A double-walled reactor having a volume of 1 L, provided with baffles, condenser, top stirrer, thermometer and dropping funnel was charged with 600 g of clear 50% strength NaOH (7.5 mol), followed by cooling to 10° C. Then 30 g of Aliquat 336 (74 mmol) and 48.2 g (0.73 mol) of freshly cracked cyclopentadiene were added. The reaction mixture was stirred turbulently for a few minutes. Then 200 g of 2-butyl bromide (1.46 mol) were added over a period of half an hour, cooling with water taking place at the same time. After 2 hours' stirring at room temperature the reaction mixture was warmed to 60° C., followed by a further 4 hours' stirring. GC was used to show that at that instant more than 90% of di(2-butyl)cyclopentadiene were present in the mixture. The product was distilled at 20 mbar and 80–90° C. After distillation, 90.8 g of di(2-butyl)cyclopentadiene were obtained. Characterization took place with the aid of GC, GC-MS, $^{13}$C- and $^{1}$H-NMR.

EXAMPLE VIII

Preparation of tri(2-butyl)cyclopentadiene

A double-walled reactor having a volume of 1 L, provided with baffles, condenser, top stirrer, thermometer and dropping funnel was charged with 400 g of clear 50% strength NaOH (5 mol). Then 9.6 g of Aliquat 336 (24 mmol) and 15.2 g (0.23 mol) of freshly cracked cyclopentadiene were added. The reaction mixture was stirred turbulently for a few minutes. Then 99.8 g of 2-butyl bromide (0.73 mol) were added over a period of half an hour, cooling with water taking place at the same time. After half an hour's stirring at room temperature the reaction mixture was warmed to 70° C., followed by a further three hours' stirring. Stirring was stopped and phase separation was awaited. The water layer was drawn off and 400 g (5.0 mol) of fresh 50% strength NaOH were added, followed by a further two hours' stirring at 70° C. GC was used to show that at that instant more than 90% of tri(2-butyl)cyclopentadiene were present in the mixture of di-, tri- and tetra(2-butyl)cyclopentadiene. The product was distilled at 1 mbar and 91° C. After distillation, 40.9 g of tri(2-butyl)cyclopentadiene were obtained. Characterization took place with the aid of GC, GC-MS, $^{13}$C- and $^{1}$H-NMR.

EXAMPLE IX

Preparation of di- and tri(2-pentyl)cyclopentadiene

A double-walled reactor having a volume of 1 L, provided with baffles, condenser, top stirrer, thermometer and dropping funnel was charged with 900 g (11.25 mol) of clear 50% strength NaOH. Then 31 g of Aliquat 336 (77 mmol) and 26.8 g (0.41 mol) of freshly cracked cyclopentadiene were added. The reaction mixture was stirred turbulently for a few minutes. Then 155 g of 2-pentyl bromide (1.03 mol) were added over a period of 1 hour, cooling with water taking place at the same time. After 3 hours' stirring at room temperature the reaction mixture was warmed to 70° C., followed by a further 2 hours' stirring. Stirring was stopped and phase separation was awaited. The water layer was drawn off and 900 g (11.25 mol) of fresh 50% strength NaOH were added, followed by a further two hours' stirring at 70° C. GC was used to show that at that instant the mixture consisted of di- and tri(2-pentyl)cyclopentadiene (approximately 1:1). The products were distilled at 2 mbar, 79–81° C. and 0.5 mbar, 102° C., respectively. After distillation, 28 g of di- and 40 g of tri(2-pentyl) cyclopentadiene were obtained. Characterization took place with the aid of GC, GC-MS, 13C- and $^{1}$H-NMR.

EXAMPLE X

Preparation of di(2-propyl) cyclohexylcyclopentadiene

In a double-walled reactor having a volume of 200 mL, provided with baffles, condenser, top stirrer, thermometer and dropping funnel, 150 g of clear 50% strength NaOH (1.9 mol), 7 g of Aliquat 336 (17.3 mmol) and 8.5 g (0.13 mol) of freshly cracked cyclopentadiene were combined. The reaction mixture was stirred turbulently at a speed of 1385 rpm for a few minutes. Then 31.5 g of 2-propyl bromide (0.26 mol) were added, cooling with water taking place at the same time. Metering in took a total time of 1 hour. After addition of the bromide the reaction mixture was warmed to 50° C. After 2 hours, stirring was stopped and phase separation was awaited. The water layer was drawn off, and 150 g (1.9 mol) of fresh 50% strength NaOH were added. This was followed by the addition of 20.9 g (0.13 mol) of cyclohexyl bromide, and stirring then continued for a further 3 hours at 70° C. GC was used to show that at that instant 80% of di(2-propyl)cyclohexylcyclopentadiene were present in the mixture. The product was distilled at 0.3 mbar and 800C. After distillation, 17.8 g of di(2-propyl) cyclohexylcyclopentadiene were obtained. Characterization took place with the aid of GC, GC-MS, 13C- and $^{1}$H-NMR.

Experiment XI

Preparation of 2-(N,N-dimethylaminoethyl) tosylate in situ

To a solution, in a three-necked round-bottomed flask provided with a magnetic stirrer and a dropping funnel, of 2-dimethylaminoethanol (1 equivalent) in dry THF at −10° C. under dry nitrogen, a solution of n-butyllithium in hexane (1 equivalent) was added (metering time: 60 minutes). After the addition of all the butyllithium the mixture was brought to room temperature and stirred for 2 hours. Subsequently the mixture was cooled (−10° C.) and p-toluenesulphonyl chloride (1 equivalent) was then added, followed by 15 minutes' stirring at this temperature, before the solution was added to a cyclopentadienyl anion.

Analogously, comparable tosylates can be prepared. In a number of the following examples a tosylate is in each case coupled with alkylated Cp compounds. In the course of said coupling the required substitution reaction is also accompanied by geminal coupling. In almost all cases it was possible to separate the geminal isomers from the non-geminal isomers by conversion of non-geminal isomers into their sparingly soluble potassium salt, followed by this salt being washed with a solvent in which said salt is insoluble or sparingly soluble.

EXAMPLE XII a. Preparation of (dimethylaminoethyl) dicyclohexylcyclopentadiene To a cooled (0° C.) solution, in a 250 ml three-necked round-bottomed flask provided with a magnetic stirrer and a dropping funnel, of dicyclohexylcyclopentadiene (Example IV) (6.90 g; 30.0 mmol) in dry tetrahydrofuran (125 ml) under a nitrogen atmosphere, a solution of n-butyllithium in hexane (18.7 ml; 1.6 mol/L; 30 mmol) was added dropwise. After 24 hours' stirring at room temperature, 30.0 mmol of 2-(dimethylaminoethyl) tosylate prepared in situ were added. After 18 hours' stirring the conversion was found to be 88%, and water (100 ml) was carefully added dropwise to the reaction mixture and the tetrahydrofuran was then distilled off. The crude product was extracted with ether and the combined organic phase was then dried (sodium sulphate) and evaporated to dryness. The residue was purified on a silica gel column, which resulted in 7.4 g of (dimethylaminoethyl)dicyclohexylcyclopentadiene.

b. Synthesis of 1-(dimethylaminoethyl)-2,4-dicyclohexylcyclopentadienyltitanium(III) dichloride and [1-(dimethylaminoethyl)-2,4-dicyclohexylcyclopentadienyl]dimethyltitanium(III) [C$_5$H$_2$(C—C$_6$H$_{11}$)$_2$(CH$_2$)$_2$NMe$_2$Ti(III)Cl$_2$] and [(C$_5$H$_2$)C—C$_6$H$_{11}$)$_2$(CH$_2$)$_2$NMe$_2$Ti(III)Me$_2$]

In a Schlenk vessel, 1.37 g (4.54 mmol) of (dimethylaminoethyl)dicyclohexylcyclopentadiene were dissolved in 30 mL of diethyl ether and the solution was then cooled to −60° C. Then 2.84 mL of n-butyllithium (1.6M in hexane; 4.54 mmol) were added dropwise. The reaction mixture was slowly brought to room temperature, followed by stirring for 2 hours. After evaporation of the solvent a yellow powder remained to which 30 mL of petroleum ether were added. In a second Schlenk vessel 40 mL of tetrahydrofuran were added to 1.68 g of Ti(III)Cl$_3$.3THF (4.53 mmol). Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue 50 mL of petroleum ether were added, which was subsequently again evaporated to dryness. A green solid remained containing 1-(dimethylaminoethyl)-2,4-dicyclohexylcyclopentadienyltitanium(III) dichloride.

In a Schlenk vessel, 0.31 g (0.671 mmol) of the above-described 1-(dimethylaminoethyl)-2,4-dicyclohexylcyclopentadienyltitanium(III) dichloride was dissolved in 30 mL of diethyl ether. The solution was cooled to −60° C. and 0.73 mL (1.84M in diethyl ether; 1.34 mmol) of methyllithium was then added dropwise. The solution was slowly brought to room temperature, followed by stirring for 1 hour. Then the solvent was evaporated and the residue extracted with 40 mL of petroleum ether. The filtrate was boiled down and dried for 18 hours in vacuo. There remained 0.14 g of a black/brown oil containing [1-(dimethylaminoethyl)-2,4-dicyclohexylcyclopentadienyl]-dimethyltitanium(III).

EXAMPLE XIII a. Preparation of (dimethylaminoethyl)di(2-pentyl) cyclopentadiene To a cooled (0° C.) solution, in a 250 ml three-necked round-bottomed flask provided with a magnetic stirrer and a dropping funnel, of di-2-pentylcyclopentadiene (7.82 g; 38.0 mmol) in dry tetrahydrofuran (125 ml) under a nitrogen atmosphere, a solution of n-butyllithium in hexane (24.0 ml; 1.6 mol/L; 38 mmol) was added dropwise. After 24 hours' stirring at room temperature, 2-(dimethylaminoethyl) tosylate (38.0 mmol) prepared in situ were added. After 18 hours' stirring the conversion was found to be 92%, and water (100 ml) was carefully added dropwise to the reaction mixture and the tetrahydrofuran was then distilled off. The crude product was extracted with ether and the combined organic phase was then dried (sodium sulphate) and evaporated to dryness. The residue was purified on a silica gel column, which resulted in 8.2 g of (dimethylaminoethyl)di(2-pentyl)cyclopentadiene.

b. Synthesis of 1-(dimethylaminoethyl)-2,4-di(2-pentyl) cyclopentadienyltitanium(III) dichloride and [1-(dimethylaminoethyl)-2,4-di(2-pentyl)cyclopentadienyl]-dimethyltitanium(III) $[C_5H_2(2-C_5H_{11})_2(CH_2)_2NMe_2Ti(III)Cl_2]$ and $[C_5H_2(2-C_5H_{11})_2(CH_2)_2NMe_2Ti(III)Me_2]$ In a Schlenk vessel, 1.60 g (5.77 mmol) of (dimethylaminoethyl)di(2-pentyl)cyclopentadiene were dissolved in 40 mL of diethyl ether and the solution was then cooled to −60° C. Then 3.6 mL of n-butyllithium (1.6M in hexane; 5.77 mmol) were added dropwise. The reaction mixture was slowly brought to room temperature, followed by stirring for 2 hours. In a second Schlenk vessel 40 mL of tetrahydrofuran were added to 2.14 g of Ti(III)Cl$_3$.3THF (5.77 mmol). Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue 50 mL of petroleum ether were added, which was subsequently again evaporated to dryness. 1.60 g of a green solid remained containing 1-(dimethylaminoethyl)-2,4-di(2-pentyl) cyclopentadienyltitanium(III) dichloride.

In a Schlenk vessel, 0.33 g (0.835 mmol) of 1-(dimethylaminoethyl)di(2-pentyl) cyclopentadienyltitanium(III) dichloride was dissolved in 40 mL of diethyl ether. The solution was cooled to −60° C. and 0.90 mL of methyllithium (1.84M in diethyl ether; 1.66 mmol) was then added dropwise. The reaction mixture was slowly brought to room temperature, followed by stirring for 1 hour. Then the solvent was evaporated. The residue was extracted with 50 mL of petroleum ether, and the filtrate was then boiled down. There remained 0.24 g of a black/brown oil containing [1-(dimethylaminoethyl)-2,4-di(2-pentyl) cyclopentadienyl]dimethyltitanium(III).

EXAMPLE XIV a. Preparation of (dimethylaminoethyl)tri(2-propyl) cyclopentadiene In a dry 500 mL three-necked flask with a magnetic stirrer, a solution of 62.5 mL of n-butyllithium (1.6M in n-hexane; 100 mmol) was added under a dry nitrogen atmosphere to a solution of 19.2 g (100 mmol) of triisopropylcyclopentadiene in 250 mL of THF at −60° C. After warming to room temperature (in approximately 1 hour) stirring continued for a further 2 hours. After cooling to −60° C., a solution of (dimethylaminoethyl) tosylate (105 mmol) prepared in situ was added over a period of 5 minutes. The reaction mixture was warmed to room temperature, followed by overnight stirring. After addition of water, the product was extracted with petroleum ether (40–60° C.). The combined organic layer was dried (Na$_2$SO$_4$) and evaporated under reduced pressure. The conversion was greater than 95%. The yield of product after distillation (based on triisopropylcyclopentadiene) was approximately 55%.

b. Synthesis of [1-(dimethylaminoethyl)-2,3,5-tri(2-propyl) cyclopentadienyltitanium(III) dichloride and [1-(dimethylaminoethyl)-2,3,5-tri(2-propyl)cyclopentadienyl] dimethyltitanium(III) $[C_5H(iPr)_3(CH_2)_2NMe_2Ti(III)Cl_2]$ and $[C_5H(iPr)_3(CH_2)_2NMe_2Ti(III)Me_2]$ In a 500 mL 3-necked flask 200 mL of petroleum ether were added to 8.5 g (28.18 mmol) of the potassium 1-(dimethylaminoethyl)-2,3,5-tri(2-propyl) cyclopentadienyl.

In a second (1 L) 3-necked flask, 300 ml of tetrahydrofuran were added to 10.5 g (28.3 mmol) of Ti(III)Cl$_3$.3THF. Both flasks were cooled to −60° C. and the organopotassium compound was then added to the Ti(III)Cl$_3$ suspension. The reaction mixture containing 1-(dimethylaminoethyl)-2,3,5-tri(2-propyl)cyclopentadienyltitanium(III) dichloride was slowly brought to room temperature, stirring continuing for a further 18 hours. This was followed by cooling to −60° C. and 30.6 mL of methyllithium (1.827M in diethyl ether, 55.9 mmol) were then added. After 2 hours' stirring at room temperature, the solvent was removed and the residue was dried in vacuo for 18 hours. To the product, 700 mL of petroleum ether were then added, followed by filtration. The filtrate was boiled down and dried in vacuo for 2 days. There remained 9.2 g of a brown/black oil containing [1-(dimethylaminoethyl)2,3,5-tri(2-propyl)cyclopentadienyl] dimethyltitanium(III).

EXAMPLE XV a. Preparation of (di-n-butylaminoethyl)di(2-pentyl) cyclopentadiene The reaction is carried out in a manner identical to that for (dimethylaminoethyl)-di-(2-pentyl)cyclopentadiene, the tosylate of N,N-di-n-butylaminoethanol being prepared in situ. The conversion was 88%. The (di-n-butylaminoethyl)-di-(2-pentyl)cyclopentadiene was obtained after preparative column purification on silica gel using, successively, petroleum ether (40–60° C.) and THF, followed by distillation under reduced pressure, the yield being 51%.

b. Preparation of 1-(di-n-butylaminoethyl)-2,4-di(2-pentyl) cyclopentadienyltitanium(III) dichloride $[C_5H_2(2-C_5H_{11})_2(CH_2)_2N(n-C_4H_9)_2Ti(III)Cl_2]$ In a Schlenk vessel, 0.919 g (2.54 mmol) of (di-n-butylaminoethyl)di(2-pentyl)cyclopentadiene was dissolved in 40 mL of diethyl ether and the solution was then cooled to −60° C. 1.6 mL of n-butyllithium (1.6M in hexane; 2.56 mmol) was then added dropwise. The reaction mixture was slowly brought to room temperature, followed by 2 hours' stirring. This was then added, at −60° C., to 960 mg (2.59 mmol) of Ti(III)Cl$_3$.3THF in 20 mL of tetrahydrofuran. The reaction mixture was then stirred for 18 hours at room temperature, after which the solvent was evaporated. The residue was washed with 10 mL of [lacuna]. There remained 0.95 g of a green solid containing 1-(di-n-butylaminoethyl)-2,4-di(2-pentyl)cyclopentadienyltitanium(III) dichloride.

EXAMPLE XVI a. Preparation of (dimethylaminoethyl)di(2-propyl) cyclopentadiene The reaction was carried out in a manner identical to that for (dimethylaminoethyl)tri(2-propyl)cyclopentadiene. The conversion was 97%. The dimethylaminoethyldiisopropylcyclopentadiene was obtained by distillation, with a yield of 54%. b. Synthesis of [1-(dimethylaminoethyl)-2,4-di(2-propyl)cyclopentadienyltitanium(III) dichloride and [1-(dimethylaminoethyl)-2,4-di(2-propyl)cyclopentadienyl] dimethyltitanium(III) [$C_5H_2(iPr)_2(CH_2)_2NMe_2Ti(III)Cl_2$] and [$C_5H_2(iPr)_2(CH_2)_2NMe_2Ti(III)Me_2$]

To 8.9 g (40.3 mmol) of (dimethylaminoethyl)-di-(2-propyl)cyclopentadiene in 100 mL of tetrahydrofuran in a 250 mL 3-necked flask, 25.2 mL of n-butyllithium (1.6M, 40.3 mmol) were added dropwise. In a second (500 mL) 3-necked flask, 100 ml of tetrahydrofuran were added to 14.93 g (40.3 mmol) of Ti(III)Cl$_3$.3THF. Both flasks were cooled to −60° C. and the organolithium compound was then added to the Ti(III)Cl$_3$ suspension. The reaction mixture containing 1-(dimethylaminoethyl)-2,4-di(2-propyl) cyclopentadienyltitanium(III) dichloride was slowly brought to room temperature, stirring continuing for a further 18 hours. This was followed by cooling to −60° C., and 50.4 mL of methyllithium (1.6M in diethyl ether; 80.6 mmol) were then added. After 2 hours' stirring at room temperature, the solvent was removed and the residue was dried in vacuo for 18 hours. To the product, 350 mL of petroleum ether were then added, followed by filtration. The filtrate was boiled down and dried in vacuo for one day. There remained 11.6 g of a brown/black oil containing [1-(dimethylaminoethyl)-2,4-di(2-propyl)cyclopentadienyl] dimethyltitanium(III).

EXAMPLE XVII a. Preparation of (dimethylaminoethyl)di(2-butyl) cyclopentadiene To a cooled (0° C.) solution, in a 250 ml three-necked round-bottomed flask provided with a magnetic stirrer and a dropping funnel, of di-(2-butyl)cyclopentadiene (8.90 g; 50.0 mmol) in dry tetrahydrofuran (150 ml) under a nitrogen atmosphere, a solution of n-butyllithium in hexane (31.2 ml; 1.6 mol/L; 50 mmol) was added dropwise. After 24 hours' stirring at room temperature, the 2-(dimethylaminoethyl) tosylate (50.0 mmol) was added. After 18 hours' stirring the conversion was found to be 96%, and water (100 ml) was carefully added dropwise to the reaction mixture and the tetrahydrofuran was then distilled off. The crude product was extracted with ether and the combined organic phase was then dried (sodium sulphate) and boiled down. The residue was purified on a silica gel column, which resulted in 8.5 g of (dimethylaminoethyl)di(2-butyl)cyclopentadiene.

b. Synthesis of 1-(dimethylaminoethyl)-2,4-di(2-butyl) cyclopentadienyltitanium(III) dichloride and [1-(dimethylaminoethyl)-2,4-di(2-butyl)cyclopentadienyl] dimethyltitanium(III) [$C_5H_2(2-C_4H_9)_2(CH_2)_2NMe_2Ti(III)Cl_2$] and [$C_5H_2(2-C_4H_9)_2(CH_2)_2NMe_2Ti(III)Me_2$]

In a Schlenk vessel, 2.36 g (9.48 mmol) of (dimethylaminoethyl)di(2-butyl)cyclopentadiene was dissolved in 50 mL of diethyl ether and the solution then cooled to −60° C. Then 5.9 mL of n-butyllithium (1.6M in hexane; 9.44 mmol) were added dropwise. The reaction mixture was slowly brought to room temperature, followed by stirring for 2 hours. In a second Schlenk vessel 50 mL of tetrahydrofuran were added to 3.51 g of Ti(III)Cl$_3$.3THF (9.44 mmol). Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue 50 mL of petroleum ether were added, which was subsequently again evaporated to dryness. 2.15 g of a green solid remained containing 1-(dimethylaminoethyl)-2,4-di(2-butyl) cyclopentadienyltitanium(III) dichloride.

In a Schlenk vessel, 0.45 g (1.22 mmol) of 1-(dimethylaminoethyl)di(2-butyl) cyclopentadienyltitanium(III) dichloride was dissolved in 40 mL of diethyl ether. The solution was cooled to −60° C. and 1.33 mL of methyllithium (1.84M in diethyl ether; 2.44 mmol) were then added dropwise. The reaction mixture was slowly brought to room temperature, followed by stirring for 1 hour. Then the solvent was evaporated. The residue was extracted with 50 mL of petroleum ether, and the filtrate was boiled down. There remained 0.36 g of a black/brown oil containing [1-(dimethylaminoethyl)-2,4-di(2-butyl) cyclopentadienyl]dimethyltitanium(III).

EXAMPLE XVIII a. Preparation of (dimethylaminoethyl)tri(2-butyl) cyclopentadiene The reaction was carried out in a manner identical to that for (dimethylaminoethyl)tri(2-propyl)cyclopentadiene. The conversion was 92%. The product was obtained by distillation, with a yield of 64%.

b. Synthesis of [1-(dimethylaminoethyl)-2,3,5-tri(2-butyl) cyclopentadienyltitanium(III) dichloride and [1-(dimethylaminoethyl)-2,3,5-tri(2-butyl)cyclopentadienyl] dimethyltitanium(III) [$C_5H(2-C_4H_9)_3(CH_2)_2NMe_2Ti(III)Cl_2$] and [$C_5H(2-C_4H_9)_3(CH_2)_2NMe_2Ti(III)Me_2$]

In a 500 mL 3-necked flask 200 mL of petroleum ether were added to 6.28 g (20.6 mmol) of the potassium 1-(dimethylaminoethyl)-2,3,5-tri(2-butyl)cyclopentadienyl. In a second (1 L) 3-necked flask, 300 ml of tetrahydrofuran were added to 7.65 g (20.6 mmol) of Ti(III)Cl$_3$.3THF. Both flasks were cooled to −60° C. and the organopotassium compound was then added to the Ti(III)Cl$_3$ suspension. The reaction mixture containing 1-(dimethylaminoethyl)-2,3,5-tri(2-butyl)cyclopentadienyltitanium(III) dichloride was slowly brought to room temperature, stirring continuing for a further 18 hours. This was followed by cooling to −60° C. and 22.3 mL of methyllithium (1.827M in diethyl ether; 40.7 mmol) were then added. After 2 hours' stirring at room temperature, the solvent was removed and the residue was dried in vacuo for 18 hours. To the product, 700 mL of petroleum ether were then added, followed by filtration. The filtrate was boiled down and dried in vacuo for 2 days. There remained 7.93 g of a brown/black oil containing [1-(dimethylaminoethyl)-2,3,5-tri(2-butyl)cyclopentadienyl] dimethyltitanium(III).

EXAMPLE XIX

Preparation of (dimethylaminoethyl)di(3-pentyl) cyclopentadiene

The reaction was carried out in a manner identical to that for (dimethylaminoethyl)di(2-propyl)cyclopentadiene. The conversion was 99%. The (dimethylaminoethyl)di(3-pentyl) cyclopentadiene was obtained with a yield of 85% after preparative column purification on silica gel using, successively, petroleum ether (40–60° C.) and THF.

EXAMPLE XX

Preparation of (di-n-butylaminoethyl)-di-(3-pentyl) cyclopentadiene

The reaction was carried out in a manner identical to that for (di-n-butylaminoethyl)di(2-propyl)cyclopentadiene. The conversion was 95%. The product was obtained with a yield of 75% after preparative column purification on silica gel using, successively, petroleum ether (40–60° C.) and THF.

EXAMPLE XXI

Preparation of (2-dimethylaminoethyl)-tri-(3-pentyl) cyclopentadiene

The reaction was carried out in a manner identical to that for (dimethylaminoethyl)tri(2-propyl)cyclopentadiene. The conversion was 94%. The (2-dimethylaminoethyl)-tri-(3-pentyl)cyclopentadiene was obtained with a yield of 61% after preparative column purification on silica gel using, successively, petroleum ether (40–60° C.) and THF.

EXAMPLE XXII a. Preparation of cyclohexyl(dimethylaminoethyl)-di-(2-propyl)cyclopentadiene In a Schlenk vessel, to a solution of cyclohexyldiisopropylcyclopentadiene (9.28 g; 40.0 mmol) in dry THF (150 mL) at room temperature, a solution of n-butyllithium in hexane (25.0 mL; 1.6 mol/L; 40.0 mmol) was added dropwise. Then, in another Schlenk vessel, a solution of n-butyllithium in hexane (25.0 mL; 1.6 mol/L; 40.0 mmol) was added dropwise to a cold (−78° C.) solution of dimethylaminoethanol (3.56 g; 40.0 mmol) in THF (100 mL). After an hour and a half's stirring at room temperature, the mixture was again cooled to −78° C. and the solid tosyl chloride (8.10 g; 40.0 mmol) was added slowly. The mixture was brought to 0° C., being stirred for 5 minutes in the process, again cooled to −78° C., and the mixture from the first Schlenk vessel then added at once. After 16 hours' stirring at room temperature the conversion was 100%. After column chromatography 11.1 g of cyclohexyl (dimethylaminoethyl)-di-(2-propyl)cyclopentadiene were obtained.

b. Synthesis of 1-(dimethylaminoethyl)-4-cyclohexyl-2,5-di (2-propyl)cyclopentadienyltitanium(III) dichloride and [1-(dimethylaminoethyl)-4-cyclohexyl-2,5-di(2-propyl) cyclopentadienyl]dimethyltitanium(III) [$C_5H(c-Hex)(2-C_3H_7)_2(CH_2)_2NMe_2Ti(III)Cl_2$] and [$C_5H(c-Hex)(2-C_3H_7)_2(CH_2)_2NMe_2Ti(III)Me_2$]

To lithium (dimethylaminoethyl)cyclohexyldi(2-propyl)cyclopentadiene (2.18 g, 7.20 mmol), dissolved in 20 mL of tetrahydrofuran, a cooled slurry (−70° C.) of Ti(III)Cl$_3$.3THF (2.67 g; 7.20 mmol) in 20 mL of THF was added at −70° C. The dark-green solution formed was stirred for 72 hours at room temperature. After this had been boiled down, 30 mL of petroleum ether (40–60) were added. After evaporating to complete dryness once more, a green powder (2.37 g) was obtained, containing 1-(dimethylaminoethyl)-4-cyclohexyl-2,5-di(2-propyl)cyclopentadienyltitanium(III) dichloride [lithium chloride]. To a slurry, cooled to −70° C., of 0.63 g (1.36 mmol) of the [1-(dimethylaminoethyl)-4-cyclohexyl-2,5-di(2-propyl)cyclopentadienyltitanium(III) dichloride].[lithium chloride] obtained above in 30 mL of diethyl ether, 1.70 mL of methyllithium (1.6M in diethyl ether, (2.72 mmol) was added dropwise. The green-brown slurry immediately darkened. Then the mixture was stirred for 1 hour at room temperature, boiled down to complete dryness and dissolved in 40 mL of petroleum ether. After filtration and complete evaporation of the solvent a black powder (0.47 g, 1.22 mmol) was obtained containing 1-(dimethylaminoethyl)-4-cyclohexyl-2,5-di(2-propyl) cyclopentadienyltitanium(III)dimethyl.

EXAMPLE XXIII

Preparation of (di-n-butylaminoethyl)di(2-propyl) cyclopentadiene

The reaction was carried out in a manner identical to that for (dimethylaminoethyl)di(2-propyl)cyclopentadiene, the tosylate of N,N-di-n-butylaminoethanol being prepared in situ. The conversion was 94%. The non-geminal di-n-butylaminoethyldi(2-propyl)cyclopentadiene was obtained by distillation with a yield of 53%.

EXAMPLE XXIV

Preparation of (dimethylaminoethyl)-tri-(2-pentyl) cyclopentadiene

The reaction was carried out in a manner identical to that for (dimethylaminoethyl)tri(2-propyl)cyclopentadiene. The conversion was 90%. The non-geminal dimethylaminoethyldiisopropylcyclopentadiene was obtained by distillation, with a yield of 54%. The (dimethylaminoethyl)-tri-(2-pentyl)cyclopentadiene was obtained with a yield of 57% after preparative column purification on silica gel using, successively, petroleum ether (40–60° C.) and THF.

EXAMPLE XXV

Preparation of bis(dimethylaminoethyl) triisopropylcyclopentadiene

In a dry 500 mL three-necked flask with a magnetic stirrer, a solution of 62.5 mL of n-butyllithium (1.6M in n-hexane; 100 mmol) was added under a dry nitrogen atmosphere to a solution of 19.2 g (100 mmol) of triisopropylcyclopentadiene in 250 mL of THF at −60° C. After warming to room temperature (in approximately 1 hour) stirring continued for a further 2 hours. After cooling to −60° C., a solution of (dimethylaminoethyl) tosylate (105 mmol) prepared in situ was added over a period of 5 minutes. The reaction mixture was warmed to room temperature, followed by overnight stirring. After addition of water, the product was extracted with petroleum ether (40–60° C.). The combined organic layer was dried (Na$_2$SO$_4$) and evaporated to dryness under reduced pressure. The conversion was greater than 95%. A portion of the product thus obtained (10.1 g; 38.2 mmol) was again alkylated under the same conditions with (dimethylaminoethyl)tosylate (39.0 mmol). The bis(2-dimethylaminoethyl)triisopropylcyclopentadiene was obtained with a yield of 35% via column chromatography.

EXAMPLE XXVI a. Preparation of (dimethylaminoethyl) tricyclohexylcyclopentadiene The reaction was carried out in a manner identical to that for (dimethylaminoethyl)dicyclohexylcyclopentadiene. The conversion was 91%. The product was obtained with a yield of 80% via preparative column purification on silica gel using, successively, petroleum ether (40–60° C.) and THF as the eluent.

b. Synthesis of 1-(dimethylaminoethyl)-2,3,5-tricyclohexylcyclopentadienyltitanium(III) dichloride and [1-(dimethylaminoethyl)-2,3,5-tricyclohexylcyclopentadienyl]dimethyltitanium(III) [$C_5H(c-Hex)_3(CH_2)_2NMe_2Ti(III)Cl_2$] and [$C_5H(c-Hex)_3(C-H_2)_2NMe_2Ti(III)Me_2$]

To lithium (dimethylaminoethyl) tricyclohexylcyclopentadiene (2.11 g, 5.70 mmol), dissolved in 20 mL of tetrahydrofuran, a cooled slurry (−70° C.) of Ti(III)Cl$_3$.3THF (2.11 g, 5.70 mmol) in 20 mL of THF was added at −70° C. The dark-green solution formed was stirred for 72 hours at room temperature. After this had been boiled down, 30 mL of petroleum ether (40–60) were added. After evaporating to complete dryness once more, a mint-green powder (2.80 g) was obtained, containing 1-(dimethylaminoethyl)-2,3,5- tricyclohexylcyclopentadienyltitanium(III) dichloride. To a slurry, cooled to −70° C., of 0.50 g (0.922 mmol) of the [1-(dimethylaminoethyl)-2,3,5-tricyclohexylcyclopentadienyltitanium(III) dichloride] [lithium chloride] obtained above in 30 mL of diethyl ether, 1.15 mL of methyllithium (1.6M in diethyl ether, (1.84 mmol) was added dropwise. The green-brown slurry immediately darkened. Then the mixture was stirred for 1 hour at room temperature, boiled down to complete dryness and dissolved in 40 mL of petroleum ether. After filtration and complete evaporation of the solvent a black powder (0.40 g, 0.87 mmol) was obtained containing (dimethylaminoethyl)-tricyclohexylcyclopentadienyl-Ti(III)dimethyl.

EXAMPLE XXVII a. Preparation of (di-n-butylaminoethyl)-tri-(2-pentyl) cyclopentadiene The reaction was carried out in a manner identical to that for (di-n-butylaminoethyl)-di-(3-pentyl)cyclopentadiene. The conversion was 88%. The (2-di-n-butylaminoethyl)-tri-(2-pentyl)cyclopentadiene was obtained with a yield of 51% after preparative column purification on silica gel using, successively, petroleum ether (40–60° C.) and THF, followed by distillation under reduced pressure.

b. Synthesis of 1-(di-n-butylaminoethyl)-2,3,5-tri(2-Pentyl) cyclopentadienyltitanium(III) dichloride [$C_5H(2-C_5H_{11})_3$ $(CH_2)_2N(n-Bu)_2Ti(III)Cl_2$]

2.633 g (6.11 mmol) of (di-n-butylaminoethyl)tri-(2-pentyl)cyclopentadiene were dissolved in 50 mL of diethyl ether and cooled to −78° C. Then 3.8 mL of n-butyllithium (1.6M in hexane; 6.11 mmol) were added. After stirring for 18 hours at room temperature, the clear light-yellow solution was boiled down followed by washing once with 25 mL of petroleum ether. The solvent was then completely evaporated, leaving behind 1.58 g of a yellow oil containing lithium 1-(di-n-butylaminoethyl)-2,3,5-tri(2-pentyl) cyclopentadienyl. Then the organolithium compound was dissolved in 50 mL of tetrahydrofuran and added, at −78° C., to 9.23 g (24.9 mmol) of Ti(III)Cl$_3$.3THF in 50 mL of tetrahydrofuran. After 18 hours' stirring at room temperature a dark-green solution had formed. After this solution had been completely boiled down, 1.52 g of a green oil remained, containing 1-(di-n-butylaminoethyl)-2,3,5-tri(2-pentyl)cyclopentadienyltitanium(III) dichloride.

Polymerization experiments XXVIII–XXXVII

A. The copolymerization of ethene with propene was carried out in the following manner A stainless steel reactor of 1 liter was charged, under dry N$_2$, with 400 ml of pentamethylheptane (PMH) and 30 μmol of triethylaluminium (TEA) or trioctylaluminium (TOA) as a scavenger. The reactor was pressurized to 0.9 MPa with purified monomers and conditioned in such a way that the ratio propene:ethene in the gas above the PMH was 1:1. The reactor contents were brought to the desired temperature while being stirred.

After conditioning of the reactor, the metal complex (5 μmol) to be used as the catalyst component and the cocatalyst (30 μmol of BF$_{20}$) were premixed over a period of 1 minute and fed to the reactor by means of a pump. The mixture was premixed in approx. 25 ml of PMH in a catalyst-dispensing vessel and after-rinsing took place with approx. 75 ml of PMH, always under a dry N$_2$ flow.

During the polymerization the monomer concentrations were kept as constant as possible by means of the reactor being supplied with propene (125 liters [s.t.p.]/hour) and ethene (125 liters [s.t.p.]/hour). The reaction was monitored on the basis of the temperature trend and the progress of the monomer infeed.

After 10 minutes' polymerization the monomer feed was stopped and the solution was drawn off under pressure and collected. The polymer was dried in vacuo for 16 hours at approximately 120° C.

B. The homopolymerization of ethene and the copolymerization of ethene with octene were carried out in the following manner.

600 ml of an alkane mixture (pentamethylheptane or special boiling point solvent) were introduced as the reaction medium, under dry N$_2$, into a stainless steel reactor having a volume of 1.5 liters. When the desired amount of dry octene was introduced into the reactor (this amount can therefore also be zero). The reactor was then, with stirring, warmed to the desired temperature under a desired ethene pressure.

Into a catalyst-dispensing vessel having a volume of 100 ml, 25 ml of the alkane mixture were metered in as solvent. Herein the desired amount of an Al-containing cocatalyst was premixed over a period of 1 minute with the desired quantity of metal complex, such that the ratio Al/(metal in the complex) in the reaction mixture is equal to 2000.

This mixture was then metered into the reactor, whereupon the polymerization started. The polymerization reaction thus started was carried out isothermally. The ethylene pressure was kept constant at the set pressure. After the desired reaction time the ethene supply was stopped and the reaction mixture was drawn off and quenched with methanol.

The reaction mixture containing methanol was washed with water and HCl in order to remove residues of catalyst. Then the mixture was neutralized with NaHCO$_3$, after which the organic fraction was admixed with an antioxidant (Irganox 1076, registered trademark) in order to stabilize the polymer. The polymer was dried in vacuo for 24 hours at 70° C.

In both cases the following conditions were varied:

metal complex type and quantity of scavenger type and quantity of cocatalyst temperature The actual conditions are stated in Table I.

TABLE I

| Example | Catalyat complex from Example | Quantity of complex (μmol/ 0.5 l) | Temperature (° C.) and pressure (bar) | Scavenger | Quantity of scavenger (mmol/ 0.5 l) | Cocatalyst | Ratio Al/M or B/M | Second mononer | Yield kg/ gM*5 min) | Comonomer incorporation (m %) | Molecular weight (Mw*10³) |
|---|---|---|---|---|---|---|---|---|---|---|---|
| XXVIII | XXVI | 5 | 150 20 | TOA | 0.2 | BF20 | 2 | octene 18 gr. | 5 | — | — |

TABLE I-continued

| Example | Catalyst complex from Example | Quantity of complex (μmol/ 0.5 l) | Temperature (° C.) and pressure (bar) | Scavenger | Quantity of scavenger (mmol/ 0.5 l) | Cocatalyst | Ratio Al/M or B/M | Second monomer | Yield kg/ gM*5 min) | Comonomer incorporation (m %) | Molecular weight (Mw*$10^3$) |
|---|---|---|---|---|---|---|---|---|---|---|---|
| XXIX | XII | 5 | 150 20 | TOA | 0.2 | BF20 | 2 | octene 18 gr. | 8 | — | — |
| XXX | XIII | 10 | 150 20 | — | — | MAO | 1000 | — | 8 | — | — |
| XXXI | XVI | 10 | 120 9 | TEA | 0.02 | BF20 | 2 | propene ratio 1 | 16 | 45.3 | 23 |
| XXXII | XIII | 10 | 150 20 | — | — | MAO | 1000 | — | 8 | — | — |
| XXXIII | XIV | 10 | 60 7 | — | — | MAO | 2000 | octene 18 gr. | 90 | 19 | 310 |
| XXXIV | XIV | 5 | 150 20 | TOA | 0.4 | BF20 | 2 | — | 37 | — | — |
| XXXV | XIV | 10 | 120 9 | — | — | MAO | 1000 | propene ratio ½ | 10.4 | 46.7 | 65 |
| XXXVI | XVI | 10 | 80 7 | — | — | MAO | 2000 | octene 18 gr. | 53 | 4.7 | — |
| XXXVII | XVI | 10 | 120 9 | TEA | 0.02 | BF20 | 2 | propene ratio 1 | 16 | 45.3 | 23 |

*BF20: tetrakis(pentafluorophenyl) borate
MAO: methylaluminoxane, from Witco

What is claimed is:

1. A metal complex comprising a metal of group 4 of the Periodic System of Elements with a valency state that is below the metal's highest valency state and comprising as a ligand of the metal at least one cyclopentadiene compound comprising a polysubstituted cyclopentadiene ring compound, wherein at least one substituent on the cyclopentadiene ring is represented by the formula -RDR'$_n$, wherein R is a linking group between the cyclopentadiene ring and the DR'$_n$ group, D is a hetero atom selected from group 15 or 16 of the Periodic System of the Elements, R' is a substituent on the hetero atom, n is the number of R' groups bonded to D wherein if D originates from group 15 then n=2, and if D originates from group 16 then n=1, and wherein each R' comprises at least one member independently selected from the group consisting of hydrocarbon radicals of 1 to 20 carbon atoms which may comprise one or more hetero atoms selected from groups 14, 15, or 16 of the Periodic System, wherein at least one further substituent present on the cyclopentadiene ring is a branched alkyl group, said compound excluding geminally substituted cyclopentadiene compounds.

2. A metal complex according to claim 1, wherein two or three branched alkyl groups are present as further substituents on the cyclopentadiene ring.

3. A process for the polymerization of α-olefins comprising utilizing as at least one catalyst component a metal complex according to claim 1.

4. A process for the copolymerization of ethene with at least one other olefin comprising utilizing as at least one catalyst component a metal complex according to claim 1.

5. A process for the copolymerization of α-olefins comprising utilizing as at least one catalyst component a metal complex according to claim 1.

6. A process for the homopolymerization of an α-olefin comprising utilizing as at least one catalyst component a metal complex according to claim 1.

7. A process for the copolymerization of α-olefins comprising utilizing as at least one catalyst component a metal complex according to claim 2.

8. A process for the homopolymerization of an α-olefin comprising utilizing as at least one catalyst component a metal complex according to claim 2.

9. A process for the polymerization of α-olefins comprising utilizing as at least one catalyst component a metal complex according to claim 2.

10. A process for the copolymerization of ethene with at least one other olefin comprising utilizing as at least one catalyst component a metal complex according to claim 2.

11. A metal complex comprising a metal of group 6 through group 10 and the lanthanides of the Periodic System of Elements and comprising as a ligand of the metal at least one cyclopentadiene compound comprising a polysubstituted cyclopentadiene ring compound, wherein at least one substituent on the cyclopentadiene ring is represented by the formula -RDR'$_n$, wherein R is a linking group between the cyclopentadiene ring and the DR'$_n$ group, D is a hetero atom selected from group 15 or 16 of the Periodic System of the Elements, R' is a substituent on the hetero atom, n is the number of R' groups bonded to D wherein if D originates from group 15 then n=2, and if D originates from group 16 then n=1, and wherein each R' comprises at least one member independently selected from the group consisting of hydrocarbon radicals of 1 to 20 carbon atoms which may comprise one or more hetero atoms selected from groups 14, 15, or 16 of the Periodic System, wherein at least one further substituent present on the cyclopentadiene ring is a branched alkyl group, said compound excluding geminally substituted cyclopentadiene compounds.

12. A metal complex according to claim 11, wherein two or three branched alkyl groups are present as further substituents on the cyclopentadiene ring.

13. A process for the polymerization of α-olefins comprising utilizing as at least one catalyst component a metal complex according to claim 11.

14. A process for the homopolymerization of an α-olefin comprising utilizing as at least one catalyst component a metal complex according to claim 11.

15. A process for the copolymerization of an α-olefin comprising utilizing as at least one catalyst component a metal complex according to claim 11.

16. A process for the copolymerization of ethene with at least one other olefin comprising utilizing as at least one catalyst component a metal complex according to claim 11.

17. A process for the polymerization of α-olefins comprising utilizing as at least one catalyst component a metal complex according to claim 12.

18. A process for the homopolymerization of an α-olefin comprising utilizing as at least one catalyst component a metal complex according to claim 12.

19. A process for the copolymerization of an α-olefin comprising utilizing as at least one catalyst component a metal complex according to claim 12.

20. A process for the copolymerization of ethene with at least one other olefin comprising utilizing as at least one catalyst component a metal complex according to claim 12.

* * * * *